(12) United States Patent
Shin et al.

(10) Patent No.: US 9,355,448 B2
(45) Date of Patent: May 31, 2016

(54) METHOD AND APPARATUS FOR IMAGE REGISTRATION

(71) Applicant: SAMSUNG MEDISON CO., LTD., Hongcheon-gun, Gangwon-do (KR)

(72) Inventors: Dong-kuk Shin, Gangwon-do (KR); Jong-sik Kim, Gangwon-do (KR); Jae-moon Jo, Gangwon-do (KR); Sung-jin Choi, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 58 days.

(21) Appl. No.: 14/137,828

(22) Filed: Dec. 20, 2013

(65) Prior Publication Data

US 2014/0321726 A1 Oct. 30, 2014

(30) Foreign Application Priority Data

Apr. 25, 2013 (KR) ........................ 10-2013-0046212

(51) Int. Cl.
*G06K 9/00* (2006.01)
*G06T 7/00* (2006.01)
(Continued)

(52) U.S. Cl.
CPC ................. *G06T 7/0012* (2013.01); *A61B 6/12* (2013.01); *A61B 6/4417* (2013.01); *A61B 6/5247* (2013.01); *A61B 8/4416* (2013.01); *A61B 8/483* (2013.01); *A61B 8/5261* (2013.01); *G06T 7/0026* (2013.01); *A61B 5/0035* (2013.01); *A61B 5/055* (2013.01); *A61B 6/032* (2013.01); *A61B 6/037* (2013.01); *A61B 6/547* (2013.01); *A61B 6/583* (2013.01); *A61B 8/4245* (2013.01); *A61B 2019/5289* (2013.01); *A61B 2019/5425* (2013.01); *A61B 2019/5466* (2013.01); *G06T 2207/10072* (2013.01); *G06T 2207/10132* (2013.01); *G06T 2207/20092* (2013.01); *G06T 2207/30056* (2013.01)

(58) Field of Classification Search
CPC combination set(s) only.
See application file for complete search history.

(56) References Cited

U.S. PATENT DOCUMENTS 6,402,693 B1 6/2002 Emery
6,614,453 B1 * 9/2003 Suri et al. ...................... 715/764
(Continued)

FOREIGN PATENT DOCUMENTS

EP  1 643 444 A1   4/2006
EP  2 478 833 A1   7/2012
WO  2012/117381 A1   9/2012

OTHER PUBLICATIONS

Partial European Search Report issued in European Application No. 13189065.9-1906 dated Sep. 29, 2014.
(Continued)

*Primary Examiner* — Anand Bhatnagar
(74) *Attorney, Agent, or Firm* — McDermot Will & Emery LLP

(57) ABSTRACT

An image registering method includes extracting a first cross-section image from first volume data about a target object, which is acquired via a first image acquisition modality; displaying the first cross-section image; acquiring second volume data about the target object, the second volume data including a second cross-section image corresponding to the first cross-section image and position information of a probe, via a second image acquisition modality using the probe; and registering the first volume data with the second volume data, based on the first cross-section image, the second cross-section image, and the position information of the probe.

21 Claims, 10 Drawing Sheets

(51) Int. Cl.
*A61B 8/08* (2006.01)
*A61B 6/12* (2006.01)
*A61B 6/00* (2006.01)
*A61B 6/03* (2006.01)
*A61B 8/00* (2006.01)
*A61B 5/055* (2006.01)
*A61B 19/00* (2006.01)
*A61B 5/00* (2006.01)

(56) References Cited

U.S. PATENT DOCUMENTS

| | | | | |
|---|---|---|---|---|
| 6,775,404 | B1* | 8/2004 | Pagoulatos et al. | 382/154 |
| 6,925,319 | B2* | 8/2005 | McKinnon | 600/407 |
| 8,145,012 | B2* | 3/2012 | Meetz et al. | 382/294 |
| 8,744,211 | B2* | 6/2014 | Owen | 382/278 |
| 2004/0068170 | A1* | 4/2004 | Wang et al. | 600/407 |
| 2008/0107312 | A1* | 5/2008 | Von Berg | 382/128 |
| 2009/0097778 | A1 | 4/2009 | Washburn et al. | |
| 2012/0150034 | A1 | 6/2012 | DeFreitas et al. | |
| 2013/0053679 | A1* | 2/2013 | Owen | 600/411 |
| 2013/0184571 | A1* | 7/2013 | Wilkening et al. | 600/426 |
| 2014/0073907 | A1* | 3/2014 | Kumar et al. | 600/414 |
| 2014/0193053 | A1* | 7/2014 | Kadoury | A61B 19/52 382/131 |

OTHER PUBLICATIONS

Wein et al., "Automatic Registration and Fusion of Ultrasound with CT for Radiotherapy," Jan. 1, 2005, pp. 303-311.

Fenster A et al: "Three-Dimensional Ultrasound Imaging", Physics in Medicine and Biology, Institute of Physics Publishing, Bristol GB, vol. 46, No. 5, May 1, 2881 (2881-85-01), XP801205497, ISSN: 0031-9155, DOI: 10.1888/0031-9155/46/5/201.

Zhe Wang et al: Registration of Ultrasound Images Using an Information-Theoretic Feature Detector, Biomedical Imaging: From Nano to Macro, 2007. ISBI 2007. 4th IEEE International Symposium on, IEEE, PI, Apr. 1, 2007, pp. 736-739, XP031084379, ISBN: 978-1-4244-0671-5.

Shuang Gao et al: "A comparision of two similarity measures in intensity-based ultrasound image registration", Proceedings I 2004 IEEE International Symposium on Circuits and Systems : May 23-26, 2004, Sheraton Vancouver Wall Centre Hotel, Vancouver, British Columbia, Canada, IEEE Operations Center, Piscataway, NJ, May 23, 2004, pp. 61-64, XP010719737, ISBN: 978-0-7803-8251-0.

Extended European Search Report issued in Application No. 13189065.9 dated Feb. 13, 2015.

* cited by examiner

METHOD AND APPARATUS FOR IMAGE REGISTRATION

CROSS-REFERENCE TO RELATED PATENT APPLICATION

This application claims the benefit of Korean Patent Application No. 10-2013-0046212, filed on Apr. 25, 2013, in the Korean Intellectual Property Office, the disclosure of which is incorporated herein in its entirety by reference.

BACKGROUND

1. Field

One or more embodiments of the present invention relate to a method and apparatus for image registration, and more particularly, to a user-friendly image registration method and apparatus that enables fast and accurate image registration.

2. Description of the Related Art

Image registration is a process of transforming different images into a common coordinate space. Image registration may denote reconstruction of at least two images into a single synthesized image. A user may ascertain the correspondence between different images, according to image registration.

In the field of diagnosis based on medical images, image registration is widely used in order to compare images of a diseased body part with each other according to the time and to compare an image of the diseased body part with an image of normal tissue. In diagnosis, in order to use an image, which is obtained by increasing strengths of or remedying weaknesses of different image acquisition modalities, image registration is used in which acquired images are represented in a same space to facilitate comparison therebetween.

For example, when a lung or a stomach is filled with air, an ultrasonic diagnosis device, a computed tomography (CT) diagnosis device, and a magnetic resonance imaging (MRI) diagnosis device have difficulty in diagnosing a lesion when only medical images of the lung or stomach are viewed. There is therefore need for an image registration system capable of performing image registration between a medical image provided by a photographing device inserted into a region of interest (ROI) of a target object and a medical image provided by an ultrasonic diagnosis device, a CT diagnosis device, or an MRI diagnosis device.

In addition, an ultrasound imaging system has noninvasive and nondestructive characteristics and is thus widely used in the medical field for obtaining information about the inside of a target object. Since an ultrasound imaging system is capable of providing a high-resolution image of the inside of a target object to doctors in real time without having to perform a surgical operation of making an incision in the target object and observing it, the ultrasound imaging system is widely in use in the medical field. However, since an ultrasonic image has a low signal-to-noise ratio (SNR), an image registration system for performing image registration between a CT image and an ultrasonic image is needed to address this problem.

An image registration method and apparatus capable of quickly providing an accurately registered image is needed by a user to accurately diagnose a disease.

SUMMARY

In the conventional art, a method of registering different sets of image data by finding at least one of corresponding points, corresponding planes, and corresponding volumes between different image data sets is used. Thus, according to such a conventional image registration method, a user should directly select at least one of a specific point, a specific plane, and a specific volume, in consideration of a direction of a target object. In addition, it takes a relatively long time for a user to directly search for and select at least one of a specific point, a specific plane, and a specific volume that is expected to be suitable for registration.

Moreover, the quality of registration greatly depends on at least one of which point, which plane, and which volume is selected from different image data sets to serve as a basis for registration. When a low-quality registration result is obtained, image registration needs to be performed again to obtain a high-quality registration result. This repetition of image registration is cumbersome and increases a processing time period.

To address these drawbacks of the conventional art, one or more embodiments of the present invention provide a user-friendly image registration method and apparatus that enables fast and accurate image registration.

According to one or more embodiments of the present invention, there is provided an image registering method comprising: extracting a first cross-section image from first volume data about a target object, which is acquired via a first image acquisition modality; displaying the first cross-section image; acquiring second volume data about the target object, the second volume data including a second cross-section image corresponding to the first cross-section image and position information of a probe, via a second image acquisition modality using the probe; and registering the first volume data with the second volume data, based on the first cross-section image, the second cross-section image, and the position information of the probe.

The image registering method may further include mapping information about an anatomical structure of a certain region in the target object with the target object and storing a result of the mapping.

The extracting of the first cross-section image may include receiving an input of selecting the target object from the user; acquiring information about an anatomical structure stored in correspondence to the target object; and extracting the first cross-section image from the first volume data, based on the information about the anatomical structure.

The acquiring of the second volume data may include displaying the second cross-section image; and displaying a degree of correlation between the first cross-section image and the second cross-section image.

The acquiring of the second volume data may further include, when the degree of correlation is a predetermined value or more, acquiring the second volume data based on the second cross-section image.

The acquiring of the second volume data may include acquiring a plurality of pieces of cross-section image data from the target object via the probe; acquiring information about a plurality of positions of the probe that correspond to the plurality of pieces of cross-section image data; and producing the second volume data based on the plurality of pieces of cross-section image data and the information about the plurality of positions of the probe.

The first image acquisition modality may include a computed tomography (CT) image acquisition modality, and the second image acquisition modality may include an ultrasound image acquisition modality.

The registering of the first volume data with the second volume data may include producing third volume data by registering the first volume data with the second volume data.

The image registering method may further include acquiring information about a current position of the probe; selecting a cross-section image corresponding to the information about the current position of the probe from the third volume data; and displaying the selected cross-section image.

According to one or more embodiments of the present invention, there is provided an image registering method comprising: receiving an input of selecting a target object from a user; displaying a reference image that represents information about an anatomical structure of a certain region in the selected target object; extracting a first cross-section image corresponding to the reference image from first volume data about the target object which is acquired via a first image acquisition modality; acquiring second volume data about the target object, the second volume data including a second cross-section image corresponding to the reference image and position information of the probe, via a second image acquisition modality using the probe; and registering the first volume data with the second volume data, based on the first cross-section image, the second cross-section image, and the position information of the probe.

According to one or more embodiments of the present invention, there is provided an image registering device comprising: a control unit that extracts a first cross-section image from first volume data about a target object which is acquired via a first image acquisition modality; a display unit that displays the first cross-section image; and an image processing unit that acquires second volume data about the target object, the second volume data including a second cross-section image corresponding to the first cross-section image and position information of a probe, via a second image acquisition modality using the probe, and that registers the first volume data with the second volume data based on the first cross-section image, the second cross-section image, and the position information of the probe.

The image registering device may further include a storage unit that maps information about an anatomical structure of a certain region in the target object with the target object and stores a result of the mapping.

The image registering device may further include a user input unit that receives a user input of selecting the target object from the user. The control unit may acquire information about an anatomical structure stored in correspondence to the target object and extract the first cross-section image from the first volume data based on the information about the anatomical structure.

The control unit may calculate a degree of correlation between the first cross-section image and the second cross-section image, and the display unit may further display the second cross-section image and the degree of correlation.

The image processing unit may acquire the second volume data based on the second cross-section image, when the degree of correlation is a predetermined value or more.

The image processing unit may acquire a plurality of pieces of cross-section image data from the target object via the probe, acquire information about a plurality of positions of the probe that correspond to the plurality of pieces of cross-section image data, and produce the second volume data based on the plurality of pieces of cross-section image data and the information about the plurality of positions of the probe.

The first image acquisition modality may include a computed tomography (CT) image acquisition modality, and the second image acquisition modality may include an ultrasound image acquisition modality.

The image processing unit may produce third volume data by registering the first volume data with the second volume data.

The control unit may acquire information about a current position of the probe and selects an image corresponding to the information about the current position of the probe from the third volume data, and the display unit may display the selected image.

According to one or more embodiments of the present invention, there is provided an image registering device including a user input unit that receives an input of selecting a target object from a user; a display unit that displays a reference image that represents information about an anatomical structure of a certain region in the selected target object; a control unit that extracts a first cross-section image corresponding to the reference image from first volume data about the target object which is acquired via a first image acquisition modality; and an image processing unit that acquires second volume data about the target object, the second volume data including a second cross-section image corresponding to the reference image and position information of a probe, via a second image acquisition modality using the probe, and that registers the first volume data with the second volume data based on the first cross-section image, the second cross-section image, and the position information of the probe.

According to one or more embodiments of the present invention, there is provided a non-transitory computer-readable recording medium having recorded thereon a computer program, which, when executed by a computer, performs any one of the above-described methods.

BRIEF DESCRIPTION OF THE DRAWINGS

The above and other features will become more apparent by describing in detail exemplary embodiments thereof with reference to the attached drawings in which.

DETAILED DESCRIPTION

Figure 1:
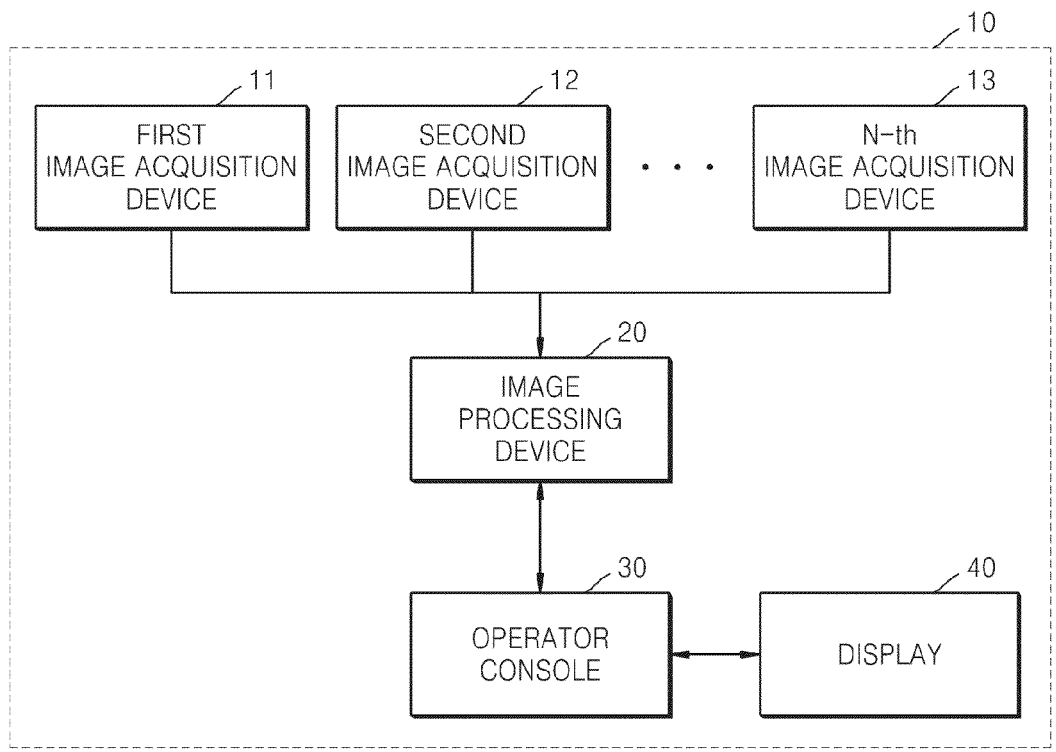
FIG. 1 is a block diagram of an example of a general diagnostic system.

Embodiments of the present invention are described in detail herein with reference to the accompanying drawings so that this disclosure may be easily performed by one of ordinary skill in the art to which the present invention pertains. The invention may, however, be embodied in many different forms and should not be construed as being limited to the embodiments set forth herein. In the drawings, parts irrelevant to the description are omitted for simplicity of explanation, and like numbers refer to like elements throughout.

In the entire specification, when an element is referred to as being "connected" or "coupled" to another element, it can be directly connected or coupled to the other element, or can be electrically connected or coupled to the other element with intervening elements interposed therebetween. In addition, the terms "comprises" and/or "comprising" or "includes" and/or "including" when used in this specification, specify the presence of stated elements, but do not preclude the presence or addition of one or more other elements. Expressions such as "at least one of," when preceding a list of elements, modify the entire list of elements and do not modify the individual elements of the list.

Throughout the specification, a "target object" may denote a living thing or an inanimate object that an image is to represent. The target object may denote a part of a human body. For example, the target object may be an organ (for example, a liver, a heart, a womb, a brain, a breast, or an abdomen) or a fetus, or may be a cross-section of a human body. Throughout the specification, a "user" may be a medical expert, such as a doctor, a nurse, a medical technologist, a sonographer, or a medical image expert, but the present invention is not limited thereto. Throughout the specification, an "image" may be an ultrasonic image, a magnetic resonance (MR) image, a computerized tomography (CT) image, a Positron Emission Tomography (PET) image, or the like, but the present invention is not limited thereto.

The present invention will now be described more fully with reference to the accompanying drawings, in which exemplary embodiments of the invention are shown.

FIG. 1 is a block diagram of a general diagnostic system 10 using image registration technology.

Referring to FIG. 1, the general diagnostic system 10 may include a first image acquisition device 11, a second image acquisition device 12, an N-th image acquisition device 13, an image processing device 20, an operator console 30, and a display 40.

The general diagnostic system 10 may be configured to acquire image data from a target object (not shown) via at least one image acquisition device. Referring to FIG. 1, the general diagnostic system 10 is configured to acquire image data via the first image acquisition device 11, the second image acquisition device 12, and the N-th image acquisition device 13.

The first image acquisition device 11 acquires a first image data set from the target object, the second image acquisition device 12 acquires a second image data set from the same target object, and the N-th image acquisition device 13 acquires an N-th image data set from the same target object.

The general diagnostic system 10 may acquire a plurality of different pieces of image data from the same target object by using various image acquisition modalities. For example, the general diagnostic system 10 may acquire computerized tomography (CT) image data, positron emission tomography (PET) image data, ultrasound image data, X-ray image data, magnetic resonance (MR) image data, optical image data, or a combination thereof, via the first image acquisition device 11, the second image acquisition device 12, and the N-th image acquisition device 13.

The image processing device 20 may process a plurality of image data sets acquired by a plurality of image acquisition devices, namely, the first, second, and N-th image acquisition devices 11, 12, and 13. For example, the image processing device 20 may register the plurality of image data sets acquired by the first, second, and N-th image acquisition devices 11, 12, and 13.

The operator console 30 may facilitate displaying of a registered image generated by the image processing device 20 or an image acquired by at least one of the first, second, and N-th image acquisition devices 11, 12, and 13, on the display 40.

The general diagnostic system 10 of FIG. 1 uses a method of registering image data sets by finding at least one of corresponding points, corresponding planes, and corresponding volumes between different image data sets based on a user input.

Thus, according to such a conventional image registration method, a user should personally select at least one of a specific point, a specific plane, and a specific volume, in consideration of a direction of a target object. In addition, it takes a relatively long time for a user to directly search for and select at least one of a specific point, a specific plane, and a specific volume that is expected to be suitable for registration.

Moreover, the quality of registration greatly depends on at least one of which point, which plane, and which volume is selected from different image data sets to serve as a basis for registration. When a low-quality registration result is obtained, image registration needs to be performed again to obtain a high-quality registration result. This repetition of image registration is cumbersome and increases a processing time period.

Figure 2:
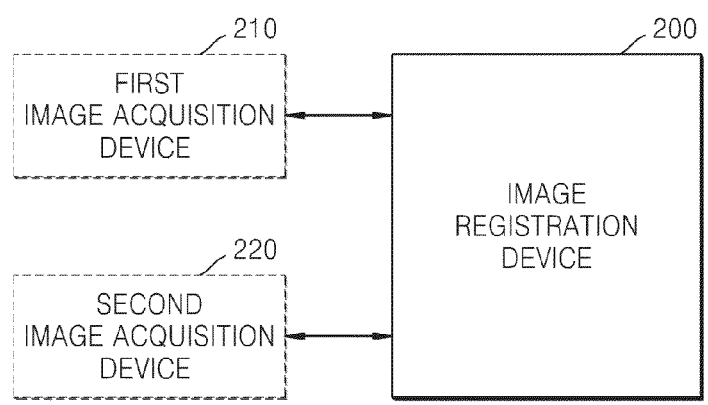
FIG. 2 is a block diagram of an image registration system according to an embodiment of the present invention.

FIG. 2 is a block diagram of an image registration system that uses an image registration device 200 according to an embodiment of the present invention.

Referring to FIG. 2, the image registration system according to the present embodiment may include the image registration device 200, a first image acquisition device 210, and a second image acquisition device 220. The image registration device 200 of FIG. 2 may correspond to the image processing device 20 of FIG. 1. The image registration device 200 may include the operator console 30 and the display 40 illustrated in FIG. 1.

The first and second image acquisition devices 210 and 220 may be different devices separated from each other, or the same devices, or devices connected to each other. The first or second image acquisition device 210 or 220 may be separated from the image registration device 200, may be included in the image registration device 200, or may be connected to the image registration device 200 by wire or wirelessly.

The first image acquisition device 210 may acquire first volume data from a target object according to a first image acquisition modality, and the second image acquisition device 220 may acquire second volume data from the target object according to a second image acquisition modality.

The first image acquisition modality and the second image acquisition modality may be the same as each other or different from each other. For example, the first image acquisition modality or the second image acquisition modality may include an ultrasonic image acquisition modality, an MR image acquisition modality, a CT image acquisition modality, a PET image acquisition modality, an X-ray image acquisition modality, an optical image acquisition modality, or a combination thereof.

To facilitate understanding of the present invention, a CT image acquisition device is illustrated as the first image acquisition device 210, and an ultrasound image acquisition device is illustrated as the second image acquisition device 220. However, the present invention is not limited thereto.

The image registration device 200 may include an ultrasound image acquisition device, but a CT image acquisition device may not be included in the image registration device 200 but may be outside the image registration device 200.

In this case, the image registration device 200 may receive CT volume data from the external CT image acquisition device. The image registration device 200 may acquire ultrasound volume data by using the ultrasound image acquisition device included therein. The image registration device 200 may register the received CT volume data with the acquired ultrasound volume data.

The image registration device 200 may select a cross-section image serving as a basis for registration from each of the first volume data and the second volume data, in order to register the first volume data and the second volume data.

For example, the image registration device 200 may select a first cross-section image as the cross-section image serving as a basis for registration from the first volume data, and may select a second cross-section image as the cross-section image serving as a basis for registration from the second volume data. The image registration device 200 may perform image registration between the first cross-section image and the second cross-section image to acquire a transform function. The image registration device 200 may register the first volume data with the second volume data based on the transform function.

According to an embodiment of the present invention, the image registration device 200 may previously set and store a cross-section image serving as a basis for registration, according to target objects from each of which volume data is to be obtained.

A cross-section image serving as a basis for registration for each target object may include a cross-section image from which a three-dimensional (3D) position of a corresponding cross-section can be identified within the volume data. For example, the cross-section image serving as a basis for registration may be a cross-section image including an image in which at least two structures cross each other. The term "structure" may be a cell, tissue, or an organ included in a living body.

Based on a user input of selecting a target object, the image registration device 200 may select a cross-section image serving as a basis for registration that is pre-stored for a selected target object, from the volume data.

According to an embodiment, the image registration device 200 may previously set and store cross-section images serving as a basis for registration, according to applications used by the image registration device 200.

The term "application" may include all sorts of application software that the image registration device 200 uses to acquire and process an image.

For example, the image registration device 200 may be configured to use different applications according to medical departments or diagnosis body parts that use registered images. Examples of the medical departments may include Obstetrics (OB), GYNecology (GYN), PeDiatrics (PD), ChestSurgery (CS), Radiology (RD), and NeuroSurgery (NS). The image registration device 200 may automatically or manually select and use a certain application from among a plurality of applications according to medical departments or diagnosis body parts.

Based on a user input of selecting an application, the image registration device 200 may select a cross-section image serving as a basis for registration pre-stored for a selected application, from the volume data.

According to an embodiment, the image registration device 200 may select a cross-section image serving as a basis for registration, based on a user input. For example, the image registration device 200 may provide a list of cross-section images corresponding to a body part input by a user (or an application selected by a user). The image registration device 200 may receive a cross-section image selected from the cross-section image list.

According to another embodiment, the image registration device 200 may select a pre-set cross-section image as the cross-section image serving as a basis for registration. For example, the image registration device 200 may automatically select a cross-section image allowing a high-quality registration result to be obtained via an experiment or a calculation, as the cross-section image serving as a basis for registration.

The image registration device 200 may increase the quality of registration by previously setting and storing, as the cross-section image serving as a basis for registration, a cross-section enabling a high-quality registration result to be obtained, according to applications or target objects. In addition, the image registration device 200 may reduce the time taken for a user to search for a cross-section image serving as a basis for registration, by automatically setting a cross-section image serving as a basis for registration for each volume data. According to an embodiment, the image registration device 200 may increase the speed of execution of image registration by reducing the time taken for a user to search for a cross-section image serving as a basis for registration.

A method in which the image registration device 200 extracts the first cross-section image from the first volume data will now be described in detail with reference to FIG. 3.

Figure 3:
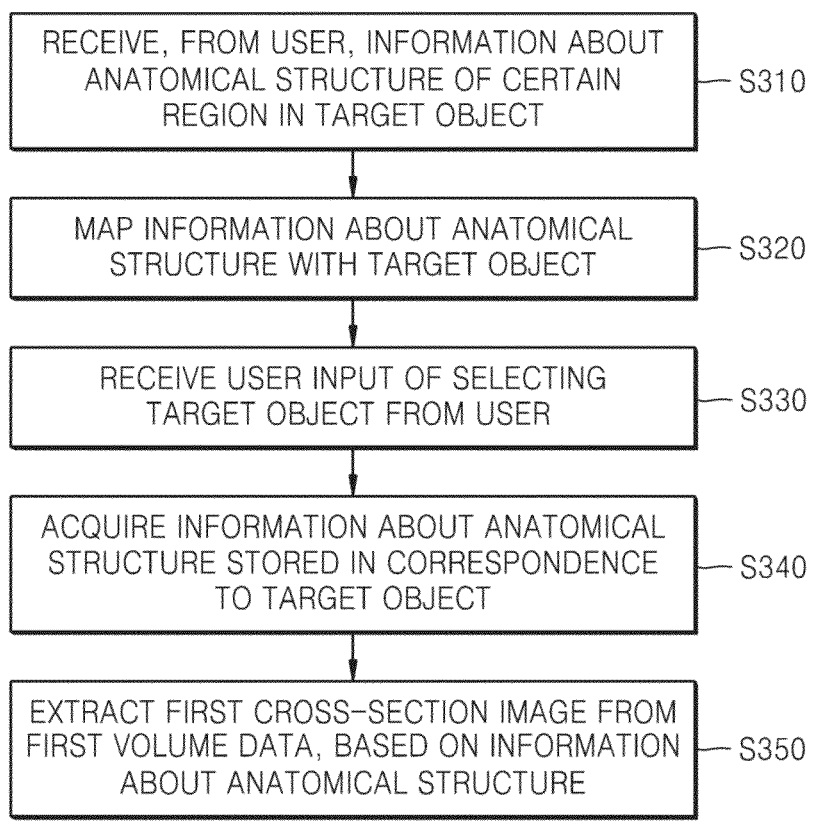
FIG. 3 is a flowchart of a method of extracting a first cross-section image from first volume data, according to an embodiment of the present invention.

FIG. 3 is a flowchart of a method of extracting the first cross-section image from the first volume data, according to an embodiment of the present invention.

In operation S310, the image registration device 200 may receive from user information about the anatomical structure of a certain region in a target object. For example, the target object may include a liver, and the certain region may include a region in the liver in which an inferior vena cava (IVC) and a portal vein cross. The anatomical structure of the certain region may include an angle formed by the IVC and the portal vein.

The information about the anatomical structure received by the image registration device 200 may include information that may be used to determine a cross-section image serving as a basis for image registration that corresponds to volume data about the target object.

For example, a cross-section image serving as a basis for image registration may include an image representative of at least two structures connected to each other at a "certain angle". Alternatively, the cross-section image serving as a basis for image registration may include an image representative of at least two structures disposed to have a "certain distance" therebetween or to have a "certain shape". Thus, the term "information about the anatomical structure" may include, for example, information about an angle formed by at least two structures, a distance between the two structures, or a configuration of the two structures within a certain cross-section image.

The image registration device 200 may receive information about a plurality of anatomical structures corresponding to a plurality of target objects. Information about an anatomical structure corresponding to a target object includes information about a certain cross-section image experimentally determined to facilitate high-quality registration, when volume data sets for the target object are registered based on the certain cross-section image. The information about an anatomical structure corresponding to a target object may include information about an anatomical structure identified within the certain cross-section image.

For example, when the target object is a liver and volume data sets are registered based on a cross-section image in which the angle formed by an IVC and a portal vein is 90 to 110 degrees, high-quality registered data may be obtained.

As another example, when the target object is a liver, the information about the anatomical structure corresponding to the target object may be "a configuration of a hepatic vein and a portal vein and an interval therebetween". When the target object is an abdomen, the information about the anatomical structure corresponding to the target object may be a configuration of a diaphragm and a vein adjacent to the diaphragm and an interval therebetween. When the target object is a thyroid, the information about the anatomical structure corresponding to the target object may be an angle at which the thyroid, a carotid, and a trachea cross each other, a configuration of the thyroid, the carotid, and the trachea, and intervals between them.

In operation S320, the image registration device 200 may map the information about the anatomical structure received in operation S310 with a target object corresponding to the information about the anatomical structure, and may store a result of the mapping. For example, "an angle formed by an IVC and a portal vein" input by a user may be allocated to a data region regarding "a liver", which is a corresponding target object, and may be stored.

In operation S330, the image registration device 200 may receive, from the user, a user input of selecting a target object. The user input of selecting a target object may include a user input of selecting an application corresponding to a target object. The image registration device 200 may automatically select the target object, based on image data input by the user.

In operation S340, the image registration device 200 may acquire information about the anatomical structure stored in correspondence to the target object selected in operation S330. The image registration device 200 may acquire the information about the anatomical structure corresponding to the target object selected in operation S330, from among a plurality of pieces of information about the anatomical structure previously stored in operation S320.

In operation S350, the image registration device 200 may extract the first cross-section image from the first volume data, based on the information about the anatomical structure acquired in operation S340.

The image registration device 200 may determine segmentation points within the first volume data about the target object, in order to extract the first cross-section image from the first volume data. A segmentation point may be a certain point, region, or volume serving as a basis for distinguishing a predetermined region in the target object from other regions. For example, the image registration device 200 may determine segmentation points corresponding to an IVC and a portal vein within the first volume data regarding a liver.

The image registration device 200 may make a frame by connecting the segmentation points to each other. The image registration device 200 may extract the first cross-section image including selected information about the anatomical structure from the first volume data, based on an angle formed by the frame.

Although a method of extracting the first cross-section image from the first volume data by using the segmentation points has been described above, the present invention is not limited thereto. Since the method in which the image registration device 200 extracts a certain cross-section image from volume data is commonly known, a detailed description thereof will be omitted.

Figure 4:
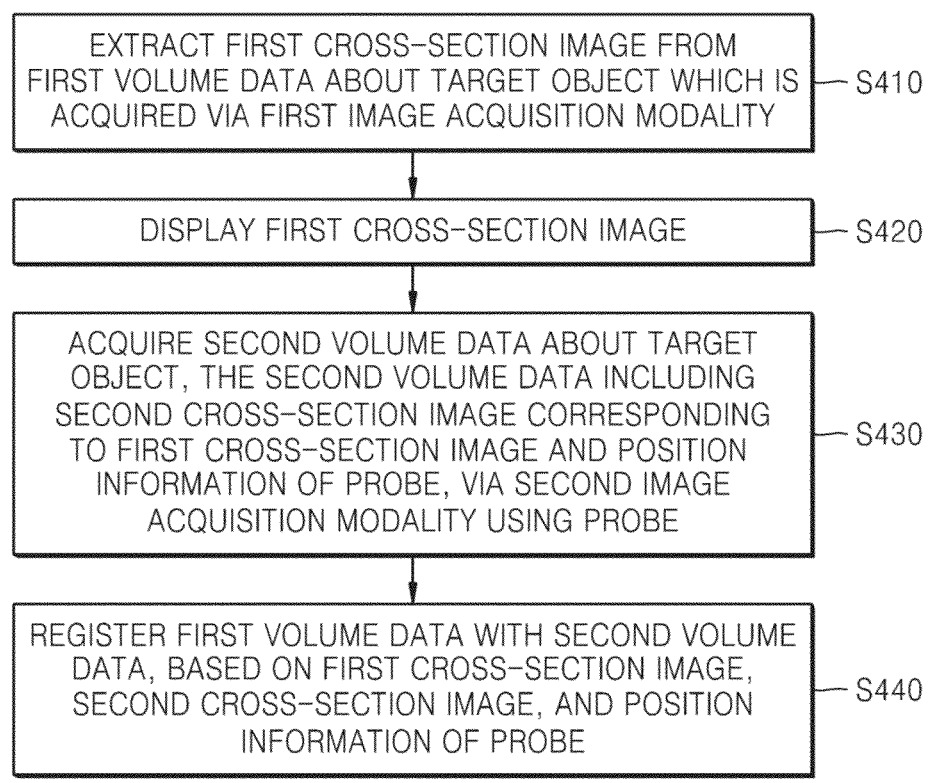
FIG. 4 is a flowchart of an image registration method according to an embodiment of the present invention.

FIG. 4 is a flowchart of an image registration method according to an embodiment of the present invention.

In operation S410, the image registration device 200 extracts a first cross-section image from first volume data about a target object, which is acquired using a first image acquisition modality. The first cross-section image may be extracted from the first volume data by using the method described above with reference to FIGS. 1 through 3. For example, the first image acquisition modality may be a CT image acquisition modality.

In operation S420, the image registration device 200 may display the first cross-section image extracted in operation S410.

As described above, the first cross-section image may be a cross-section image experimentally determined to produce high-quality registered data when image registration is performed based on the first cross-section image, compared to when image registration is performed based on the other cross-section images.

A user acquires second volume data by referring to the displayed first cross-section image, thereby increasing the accuracy of image registration. The first cross-section image that a user refers to in order to acquire the second volume data will be described later in detail with reference to FIGS. 5A and 5B, which illustrates screens on which the first cross-section image is displayed.

In operation S430, the image registration device 200 may acquire second volume data by using a second image acquisition modality using a probe. The second volume data may include a second cross-section image corresponding to the first cross-section image and information about the position of the probe. The probe included in the image registration device 200 may transmit a certain signal to the target object and may receive an echo signal reflected by the target object.

For example, the second image acquisition modality may be an ultrasound image acquisition modality. In this case, the probe generates ultrasound image data by digitizing an echo signal, which is an ultrasound signal, received from the target object.

The probe may include a two-dimensional (2D) probe capable of acquiring cross-section image data of the target object, a 3D probe capable of acquiring volume data, and a four-dimensional (4D) probe capable of acquiring both volume data and time information.

For example, the second volume data is acquired using a 2D probe as follows.

The image registration device 200 may acquire a plurality of pieces of cross-section image data from the target object via the probe, as a user moves the probe. The plurality of pieces of cross-section image data include pieces of image data that are acquired, via the probe, for a plurality of different cross-sections within the target object.

In addition, the image registration device 200 may acquire information about a plurality of positions of the probe that correspond to the pieces of cross-section image data, respectively. The information about the positions of the probe may include information about spatial positions of the probe and information about directions of the probe.

The image registration device 200 may produce second volume data based on the plurality of pieces of cross-section image data and the information about the plurality of positions of the probe. A method of acquiring the second volume data by using a 2D probe will be described later in more detail with reference to FIG. 7.

The image registration device 200 may display a second cross-section image together with the first cross-section image. The displayed second cross-section image may include an ultrasound image that is acquired in real time by the probe.

The image registration device 200 may display a degree of correlation between the first cross-section image and the second cross-section image. The degree of correlation may be calculated based on similarity between two images or similarity between segmentation points included in the two images. The degree of correlation between the first cross-section image and the second cross-section image may be displayed in the form of a character, an image, or a symbol.

When the degree of correlation between the first cross-section image and the second cross-section image is a predetermined value or greater, the image registration device 200 may acquire the second volume data based on the second cross-section image. In other words, when the degree of correlation between the first cross-section image and the second cross-section image is a predetermined value or greater, the image registration device 200 may automatically set the second cross-section image as a reference image for acquiring the second volume data. The predetermined value may be a value input by a user, or may be a value pre-stored in the image registration device 200.

The second volume data acquired based on the second cross-section image may include volume data obtained by reconstructing a plurality of pieces of cross-section image data based on the second cross-section image and the position of the probe that corresponds to the second cross-section image.

When the degree of correlation between the first cross-section image and the second cross-section image is a predetermined value or greater (for example, when the degree of correlation is 90% or more), the image registration device 200 may automatically perform a volume data acquiring operation. In addition, when the degree of correlation between the first cross-section image and the second cross-section image is a predetermined value or greater, the image registration device 200 may display on a screen a user interface that allows a user input for performing the volume data acquiring operation. The image registration device 200 may perform the volume data acquiring operation, based on a user's command.

In operation S440, the image registration device 200 may register the first volume data with the second volume data, based on the first cross-section image, the second cross-section image, and the information about the position of the probe.

The image registration device 200 may produce third volume data by registering the first volume data with the second volume data. For example, the image registration device 200 may register the first volume data and the second volume data by determining segmentation points that are to be included in the second cross-section image and that correspond to the segmentation points included in the first cross-section image.

The image registration device 200 may display an identifier capable of identifying the quality of registration performed to produce the third volume data. The quality of registration may be identified based on the similarity between the first volume data and the second volume data or the similarity between the segmentation points in the first volume data and the segmentation points in the second volume data.

When a user fails to obtain a satisfactory registration result, point registration in which the first volume data and the second volume data are registered based on segmentation points selected by a user may be additionally performed.

The image registration device 200 may select a certain cross-section image from the third volume data and may display the selected cross-section image. The selected cross-section image may include a cross-section image obtained by registering an image acquired via the first image acquisition modality and an image acquired via the second image acquisition modality.

In addition, the image registration device 200 may acquire information about a current position of the probe, select an image corresponding to the information about the current position of the probe from the third volume data, and display the selected image. Accordingly, the image registration device 200 may change a displayed registered image as a user moves the probe.

Figure 5A:
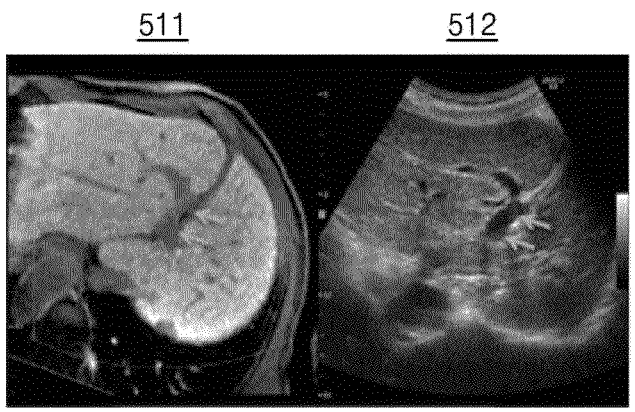
FIGS. 5A and 5B illustrate images displayed on a screen, according to an embodiment of the present invention.
Figure 5B:
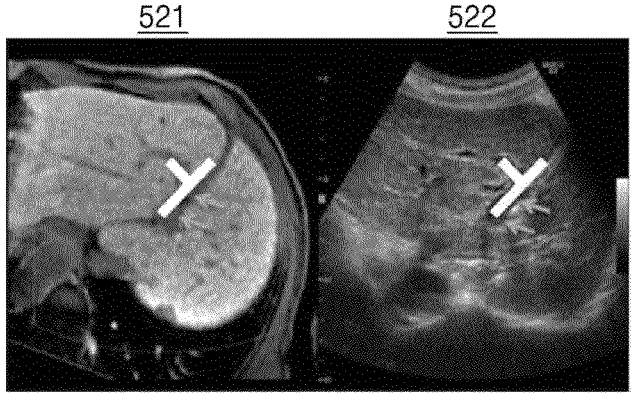

FIGS. 5A and 5B illustrate exemplary images displayed on a screen, according to an embodiment of the present invention.

The images of FIGS. 5A and 5B are images displayed by the image registration device 200 when the image registration device 200 registers volume data acquired by a CT image acquisition device with volume data acquired by an ultrasound image acquisition device.

The image registration device 200 may receive a user input of selecting an ultrasound application that is used to acquire an image of a liver. The image registration device 200 may determine that a target object for image registration is a liver, based on the user input of selecting the ultrasound application.

The image registration device 200 may search a storage unit 1150 (see FIG. 11) for information about an anatomical structure mapped with a liver. When volume data sets for a liver are registered, the storage unit 1150 may store information about a reference cross-section image used to produce high-quality registered data, in a data region corresponding to a liver. The information about the reference cross-section image may include the information about an anatomical structure represented on the reference cross-section image.

For example, when volume data regarding a liver is registered, the image registration device 200 may store information indicating that, when the volume data is registered based on an image in which an angle formed by an IVC and a portal vein is 90°, very high-quality registration data can be obtained.

The image registration device 200 may extract a first cross-section image serving as a basis for image registration from the first volume data, based on the ultrasound application, and may display the first cross-section image. The first cross-section image may include a cross-section image that is previously stored by being experimentally determined to facilitate most-accurate registration between volume data sets. The image registration device 200 may automatically extract the first cross-section image from the first volume data and may display the first cross-section image, as illustrated on an image 511 of FIG. 5A.

The image 511 of FIG. 5A is a first cross-section image including an IVC and a portal vein, which is extracted from CT volume data regarding a liver. A user may move the probe to a location from which a second cross-section image corresponding to the image 511 can be acquired, by referring to the image 511.

An image 512 of FIG. 5A is an ultrasound image acquired from a liver via the probe.

The image registration device 200 may acquire second volume data based on the image 512 corresponding to the image 511, by allowing a user to move the probe by referring to the image 511. The image registration device 200 may obtain high-quality registered data by using the second volume data acquired based on the image 512.

Images 521 and 522 of FIG. 5B are images obtained by highlighting the IVC and the portal vein on the images 511 and 512, respectively. The image registration device 200 may determine the IVC and the portal vein marked on the images 521 and 522 of FIG. 5B to be segmentation points, and may calculate a degree of correlation between the images 521 and 522 based on a similarity between the segmentation points.

Since the image registration device 200 previously stores a cross-section image enabling a high-quality registration result to be obtained, according to the ultrasound application, trial and error that may occur due to registering volume data based on an inappropriate cross-section image may be reduced. Moreover, since a user acquires second volume data based on displayed first cross-section image, the second volume data, which is to be registered with the first volume data, may be acquired by searching for a relatively-small volume. In other words, the image registration device 200 may more quickly acquire the second volume data suitable for image registration.

Figure 6:
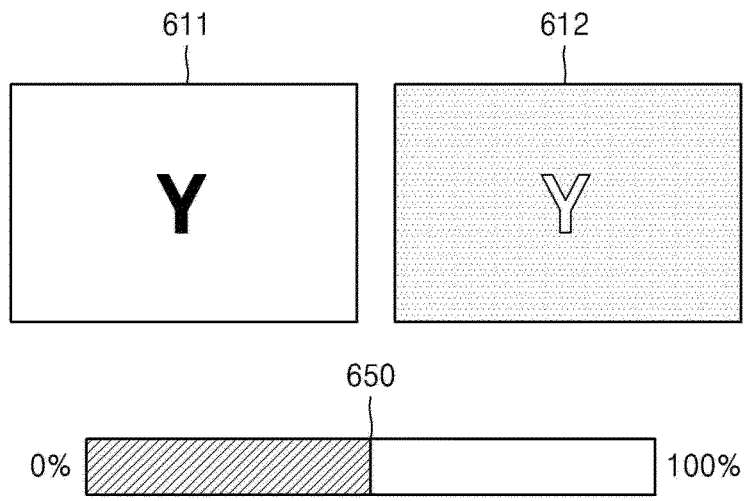
FIG. 6 illustrates an example of a screen on which a degree of correlation between a first cross-section image and a second cross-section image is displayed, according to an embodiment of the present invention.

FIG. 6 illustrates an example of a screen on which a degree of correlation between a first cross-section image and a second cross-section image is displayed, according to an embodiment of the present invention.

As illustrated in FIG. 6, the image registration device 200 may display a graphical user interface (GUI) that represents a degree of correlation between a first cross-section image 611 and a second cross-section image 612. For example, the image registration device 200 may display the degree of correlation in the form of a bar 650. Although the degree of correlation is displayed in the form of a bar in FIG. 6, the present invention is not limited thereto.

Since the image registration device 200 displays the degree of correlation between the first and second cross-section images in a GUI form, a user may intuitively know the degree of correlation between the first and second cross-section images.

Figure 7:
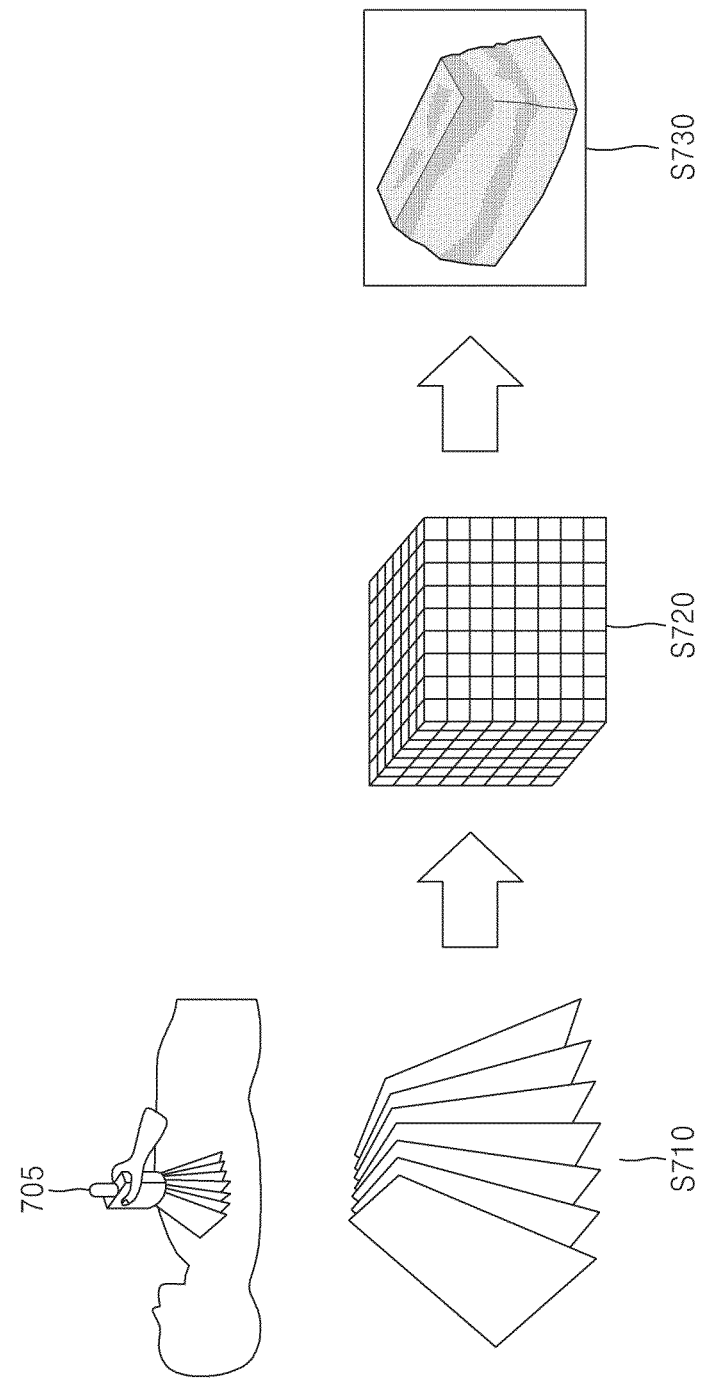
FIG. 7 is a schematic diagram for describing a method of acquiring second volume data according to a second image acquisition modality using a probe, according to an embodiment of the present invention.

FIG. 7 is a schematic diagram for describing a method of acquiring the second volume data, according to an embodiment of the present invention.

The image registration device 200 may perform a cross-section data collecting operation S710, a volume data reconstructing operation S720, and a 3D image display operation S730.

In the cross-section data collecting operation S710, the image registration device 200 may acquire a plurality of pieces of image data for a plurality of cross-sections included in a target object, while changing the position of a 2D probe. Alternatively, the image registration device 200 may acquire the plurality of pieces of image data for the plurality of cross-sections included in a target object by using a 3D probe.

For example, when a 2D probe including a positioning sensor capable of sensing position information of the 2D probe is used, acquisition of image data about a bone that is not a target object of interest may be minimized.

In the volume data reconstructing operation S720, the image registration device 200 may reconstruct volume data from the cross-section image data pieces acquired in operation S710. The cross-section image data pieces acquired in operation S710 are pieces of data respectively obtained in different coordinate systems. Accordingly, the image registration device 200 transforms the cross-section image data pieces into volume data in a common space coordinate system, based on the cross-section image data pieces and information about a plurality of positions of the probe.

If necessary, in the 3D image display operation S730, the image registration device 200 may display the volume data on a 2D screen by rendering.

Figure 8:
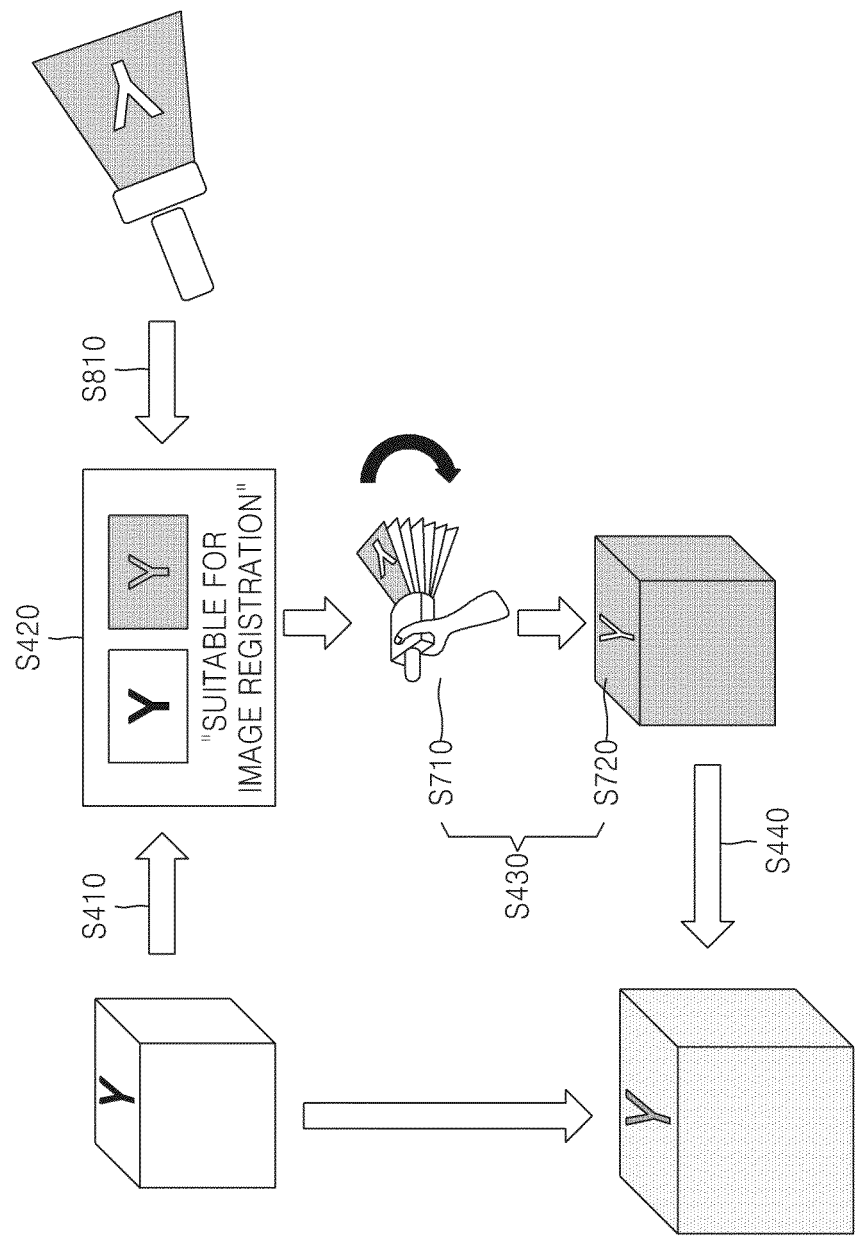
FIG. 8 is a conceptual diagram for describing an image registration method according to an embodiment of the present invention.

FIG. 8 is a conceptual diagram for describing an image registration method according to an embodiment of the present invention.

In operation S410, the image registration device 200 may extract a first cross-section image from first volume data about a target object acquired via the first image acquisition modality. In operation S420, the image registration device 200 may display the first cross-section image.

In operation S810, the image registration device 200 may display a second cross-section image that is obtained via a probe in real time, together with the first cross-section image.

When a degree of correlation between the first and second cross-section images is a predetermined value or greater, the image registration device 200 may display information indicating that the first and second cross-section images are suitable to be registered. A user may input a command instructing the image registration device 200 to perform a second volume data acquiring operation.

In operation S430, the image registration device 200 may acquire second volume data based on the second cross-section image. In operation S710, the image registration device 200 may acquire a plurality of pieces of cross-section image data and information about a plurality of positions of the probe that correspond to the plurality of pieces of cross-section image data, respectively, as the user moves the probe. In operation S720, the image registration device 200 may reconstruct the second volume data from the plurality of pieces of cross-section image data.

In operation S440, the image registration device 200 may register the first volume data with the second volume data, based on the first cross-section image, the second cross-section image, and the information about the positions of the probe.

According to the image registration method illustrated in FIG. 8, the image registration device 200 may automatically register the first volume data and the second volume data via only an operation of acquiring the second volume data as the user moves the probe. In other words, the image registration method according to the present embodiment may not need an operation of receiving a user input of selecting a cross-section suitable for image registration. Thus, according to an embodiment of the present invention, there is provided an image registration method that may be easily used by users and is simple to perform.

Figure 9:
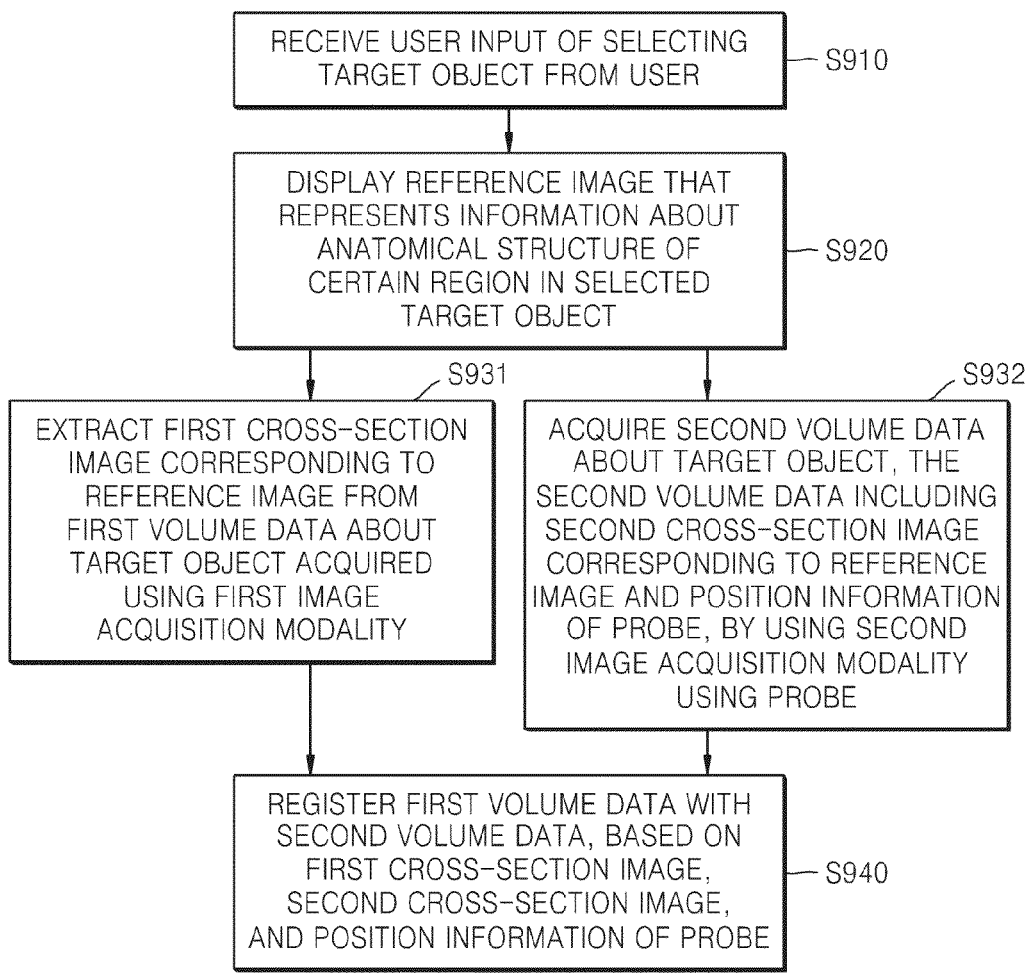
FIG. 9 is a flowchart of an image registration method according to another embodiment of the present invention.

FIG. 9 is a flowchart of an image registration method according to another embodiment of the present invention.

In operation S910, the image registration device 200 may receive a user input of selecting a target object from a user. The operation S910 of FIG. 9 corresponds to the operation S330 of FIG. 3, so a detailed description thereof will be omitted.

In operation S920, the image registration device 200 may display a reference image that represents information about the anatomical structure of a certain region in the target object selected in operation S910. The information about the anatomical structure may include information that is usable to set a cross-section image serving as a basis for image registration for volume data about the target object.

The reference image that represents the information about the selected anatomical structure may include image information or character information. For example, the reference image may include a body marker representative of the selected anatomical structure.

The body marker may denote a marker that imitates the shape of a structure included in a target object so as to identify a 3D position of a cross-section serving as a basis for registration within volume data. For example, the body marker may have the same shape as the shape in which at least two structures cross each other.

Figure 10:
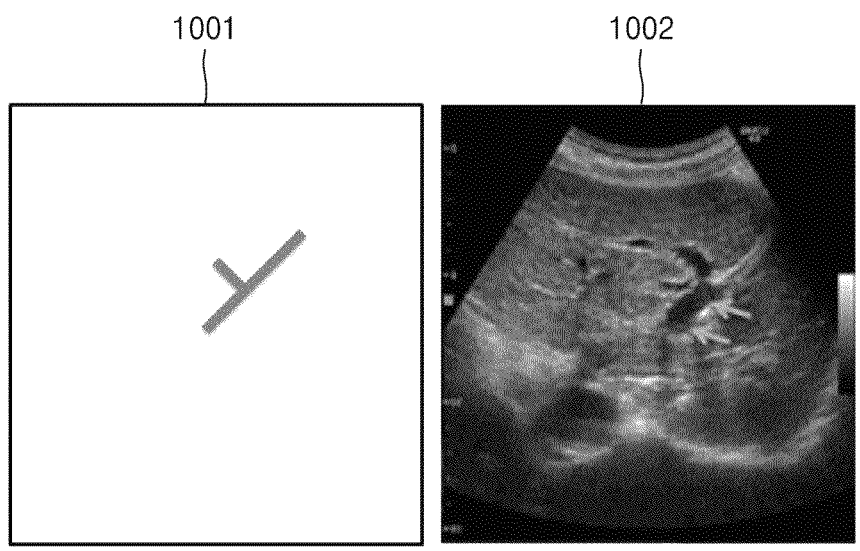
FIG. 10 illustrates images displayed on a screen, according to another embodiment of the present invention.

The reference image, for example, a reference image 1001 of FIG. 10, may also include a description of the 3D position of the cross-section serving as a basis for registration within the target object. In other words, the reference image may include a description that is concrete enough for a user to know the position of the selected anatomical structure according to the reference image.

The image registration device 200 may select information about the anatomical structure corresponding to the target object selected in operation S910, from among a plurality of pre-stored pieces of information about anatomical structures. Pre-storing the plurality of pieces of information about anatomical structures and mapping them with a plurality of target objects have been described above with reference to FIG. 2 and the operations S310 and S320 of FIG. 3.

In operation S931, the image registration device 200 may extract a first cross-section image corresponding to the reference image from first volume data about the target object acquired using a first image acquisition modality. A method of extracting the first cross-section image corresponding to the reference image from the first volume data has been described above with reference to the operation S350 of FIG. 3 or the operation S410 of FIG. 4.

In operation S932, the image registration device 200 may acquire second volume data about the target object, the second volume data including a second cross-section image corresponding to the reference image and position information of a probe, by using a second image acquisition modality using the probe. A method of acquiring the second volume data has been described above with reference to the operation S430 of FIG. 4.

In operation S940, the image registration device 200 may register the first volume data and the second volume data, based on the first cross-section image, the second cross-section image, and the position information of the probe. The operation S940 of FIG. 9 corresponds to the operation S440 of FIG. 4, so a detailed description thereof will be omitted.

FIG. 10 illustrates images displayed on a screen, according to another embodiment of the present invention.

The images of FIG. 10 are images displayed by the image registration device 200, when the image registration device 200 registers first volume data acquired via a first image acquisition modality with second volume data acquired via an ultrasound image acquisition modality.

The image registration device 200 may receive a user input of selecting an ultrasound application for acquiring an image of a liver. The image registration device 200 may determine that a target object for image registration is a liver, based on the user input of selecting the ultrasound application.

The image registration device 200 may search the storage unit 1150 of FIG. 11 for the reference image 1001 mapped with a liver. The reference image 1001 may include a body marker that represents a cross-section serving as a basis for registration, which is used to register the first volume data and the second volume data.

The reference image 1001 of FIG. 10 includes a body marker that marks an IVC and a portal vein of the liver. A user moves a probe to a location from which a second cross-section image 1002 corresponding to the reference image 1001 can be acquired, by referring to the reference image 1001. In other words, a user may move the probe to a location from which the second cross-section image 1002 including an IVC and a portal vein of the liver can be acquired.

Figure 11A:
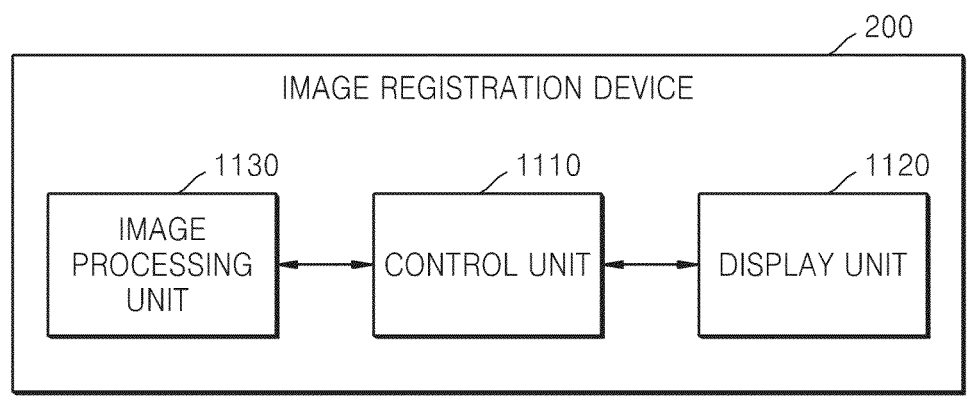
FIGS. 11A and 11B are block diagrams for describing an image registration device according to an embodiment of the present invention.
Figure 11B:
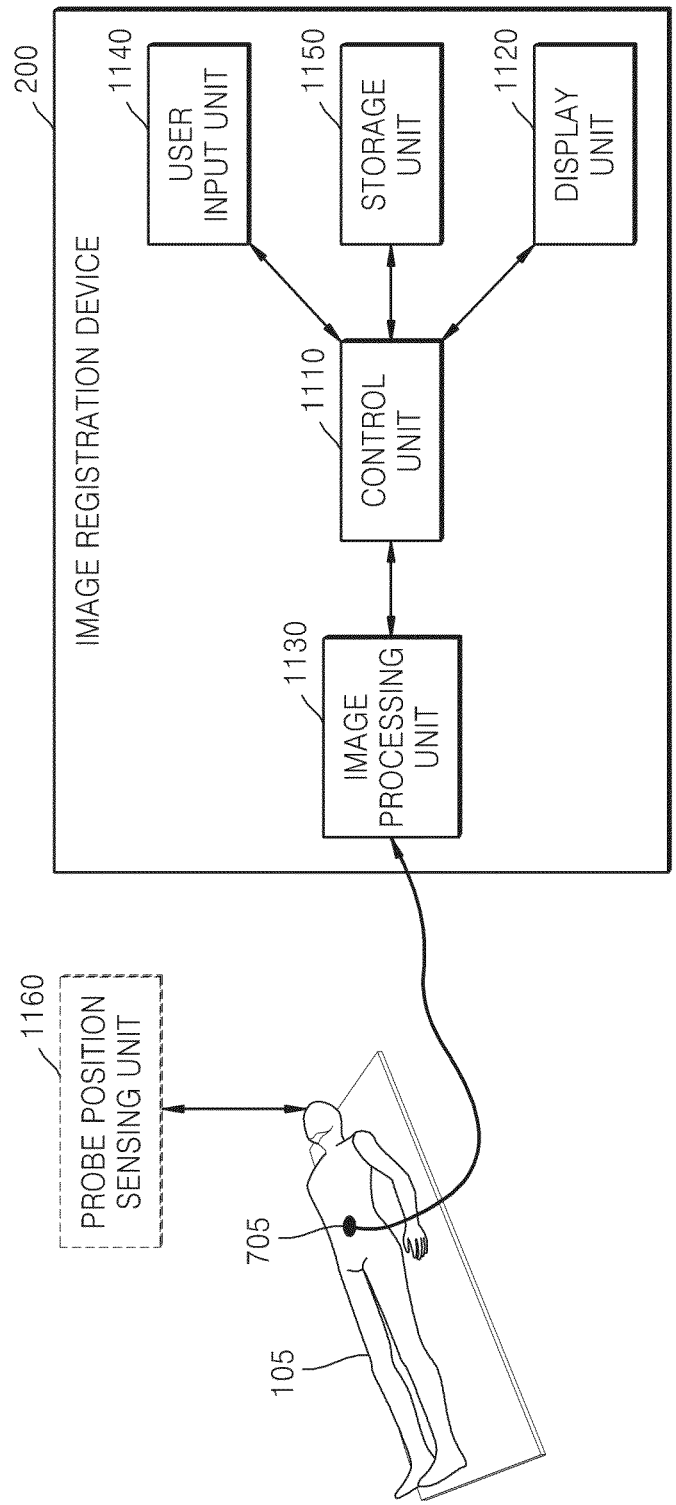

FIGS. 11A and 11B are block diagrams for describing an image registration device 200 according to an embodiment of the present invention.

Referring to FIG. 11A, the image registration device 200 includes an image processing unit 1130, a control unit 1110, and a display unit 1120.

The image registration device 200 may be realized in various forms. For example, the image registration device 200 may be implemented by using a fixed terminal or a movable terminal. Examples of the movable terminal may include a laptop computer, a personal digital assistant (PDA), and a tablet PC.

The control unit 1110 may extract a first cross-section image from first volume data about a target object 105, which is acquired via a first image acquisition modality.

The control unit 1110 may control all of the operations of the image registration device 200, and may control the image processing unit 1130 and the display unit 1120 in order to perform image registration methods according to embodiments of the present invention.

The display unit 1120 may display the first cross-section image extracted by the control unit 1110.

The display unit 1120 may also display information that is processed in the image registration device 200. For example, the display unit 1120 may display status information necessary for acquiring and registering volume data, a user interface (UI) or GUI associated with function setting, and an image of the target object 105.

When a display panel of the display unit 1120 forms a layer structure together with a touch pad, which is to be described later, to construct a touch screen, the display unit 1120 may be used as an input device as well as an output device.

The display unit 1120 may include at least one of a liquid crystal display (LCD), a thin film transistor-liquid crystal display (TFT-LCD), an organic light-emitting diode (OLED), a flexible display, a 3D display, and an electrophoretic display.

The image processing unit 1130 may acquire second volume data about the target body 105 via a second image acquisition modality using a probe 705. The second volume data may include a second cross-section image corresponding to the first cross-section image and information about the positions of the probe 705.

The image processing unit 1130 may register the first volume data and the second volume data, based on the first cross-section image, the second cross-section image, and the information about the positions of the probe 705.

Referring to FIG. 11B, the image registration device 200 may further include the probe 705, a probe position sensing unit 1160, a user input unit 1140, and the storage unit 1150.

The control unit 1110 may further control the probe 705, the probe position sensing unit 1160, the user input unit 1140, and the storage unit 1150 in order to perform image registration methods according to embodiments of the present invention. The probe position sensing unit 1160 may sense a position of the probe 705. The probe position sensing unit 1160 may be included in the probe 705. Alternatively, the probe position sensing unit 1160 may be located outside the probe 705. When the probe position sensing unit 1160 is located outside the probe 705, it may be located within a shielded room in which image capturing is performed on a target object. A method in which the probe position sensing unit 1160 senses a position of the probe 105 is commonly known, and thus, a detailed description thereof will be omitted.

The user input unit 1140 denotes a unit via which a user inputs information necessary for image registration. The user input unit 1140 may receive "information about a certain region in a target object" or "an input of selecting a target object", which is used to extract the first cross-section image from the first volume data.

The user input unit 1140 may include, but not limited to, a key pad, a dome switch, a touch pad (e.g., a capacitive overlay type, a resistive overlay type, an infrared beam type, an integral strain gauge type, a surface acoustic wave type, a piezo electric type, or the like), a jog wheel, or a jog switch. In particular, as described above, when a touch pad forms a layer structure together with a display panel, the layer structure may be referred to as a touch screen.

The storage unit 1150 stores a variety of information that the image registration device 200 needs to display information associated with image registration. For example, the storage unit 1150 may map information about the anatomical structure of a certain region in the target object 105 with the target object 105 and store a result of the mapping. The storage unit 1150 may store, for example, but is not limited to, the first volume data, the second volume data, and third volume data.

The storage unit 1150 may include at least one type of storage medium selected from among a flash memory type, a hard disk type, a multimedia card micro type, a card type memory (for example, a secure digital (SD) or extreme digital (XD) memory), a random access memory (RAM), a static random access memory (SRAM), a read-only memory (ROM), an electrically erasable programmable ROM (EEPROM), a programmable ROM (PROM), magnetic memory, a magnetic disk, and an optical disk. The image registration device 200 may operate a web storage facility or a cloud server on the internet which performs a storage function of the storage unit 1150.

According to the aforementioned image registration devices and methods according to the embodiments of the present invention, a reference image enabling a high-quality registration result to be obtained is automatically set without needing a user's operation of selecting a certain cross-section, that is, a certain plane, serving as a basis for registration, whereby a high-quality registered image may be consistently obtained.

Moreover, according to the aforementioned image registration devices and methods according to the embodiments of the present invention, a reference image is automatically set without the user inconvenience of having to personally select at least one of a specific point, a specific plane, and a specific volume serving as a basis for registration, and thus, fast and user-friendly volume-based registration may be performed.

The embodiment of the present invention can be embodied in a storage medium including instruction codes executable by a computer such as a program module executed by the computer. A computer readable medium can be any usable medium which can be accessed by the computer and includes all volatile/non-volatile and removable/non-removable media. Further, the computer readable medium may include all computer storage and communication media. The computer storage medium includes all volatile/non-volatile and removable/non-removable media embodied by a certain method or technology for storing information such as computer readable instruction code, a data structure, a program module or other data.

Although the embodiments of the present invention have been disclosed for illustrative purposes, one of ordinary skill in the art will appreciate that diverse variations and modifications are possible, without departing from the spirit and scope of the invention. Thus, the above embodiments should be understood not to be restrictive but to be illustrative, in all aspects. For example, respective elements described in an integrated form may be dividedly used, and the divided elements may be used in a state of being combined.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An image registering method comprising:
   extracting a first cross-section image from first volume data about a target object based on information about an anatomical structure stored in correspondence to the target object, wherein the first volume data is acquired via a first image acquisition modality;
   displaying the first cross-section image;
   acquiring second volume data about the target object, the second volume data including a second cross-section image corresponding to the first cross-section image and position information of a probe, via a second image acquisition modality using the probe; and
   registering the first volume data with the second volume data, based on the first cross-section image, the second cross-section image, and the position information of the probe.

2. The image registering method of claim 1, further comprising mapping information about an anatomical structure of a certain region in the target object with the target object and storing a result of the mapping.

3. The image registering method of claim 1, wherein the target object is selected by receiving an input of selecting the target object from a user.

4. The image registering method of claim 1, wherein the acquiring of the second volume data comprises:
   displaying the second cross-section image; and
   displaying a degree of correlation between the first cross-section image and the second cross-section image.

5. The image registering method of claim 4, wherein the acquiring of the second volume data comprises, when the degree of correlation is a predetermined value or more, acquiring the second volume data based on the second cross-section image.

6. The image registering method of claim 1, wherein the acquiring of the second volume data comprises:
   acquiring a plurality of pieces of cross-section image data from the target object via the probe;
   acquiring information about a plurality of positions of the probe that correspond to the plurality of pieces of cross-section image data; and
   producing the second volume data based on the plurality of pieces of cross-section image data and the information about the plurality of positions of the probe.

7. The image registering method of claim 1, wherein the first image acquisition modality comprises a computed tomography (CT) image acquisition modality, and
   the second image acquisition modality comprises an ultrasound image acquisition modality.

8. The image registering method of claim 1, wherein the registering of the first volume data with the second volume data comprises producing third volume data by registering the first volume data with the second volume data.

9. The image registering method of claim 8, further comprising:
   acquiring information about a current position of the probe;

selecting a cross-section image corresponding to the information about the current position of the probe from the third volume data; and displaying the selected cross-section image.

10. An image registering method comprising:

receiving an input of selecting a target object from a user;

determining a reference image based on information about an anatomical structure stored in correspondence to the target object;

extracting a first cross-section image corresponding to the reference image from first volume data about the target object, wherein the first volume data is acquired via a first image acquisition modality;

acquiring second volume data about the target object, the second volume data including a second cross-section image corresponding to the reference image and position information of the probe, via a second image acquisition modality using the probe; and registering the first volume data with the second volume data, based on the first cross-section image, the second cross-section image, and the position information of the probe.

11. An image registering device comprising:

a display; and one or more processors configured to:

extract a first cross-section image from first volume data about a target object based on information about an anatomical structure stored in correspondence to the target object, wherein the first volume data is acquired via a first image acquisition modality;

control the display to display the first cross-section image;

acquire second volume data about the target object, the second volume data including a second cross-section image corresponding to the first cross-section image and position information of a probe, via a second image acquisition modality using the probe; and register the first volume data with the second volume data based on the first cross-section image, the second cross-section image, and the position information of the probe.

12. The image registering device of claim 11, further comprising a storage, wherein the one or more processors are further configured to:

map information about an anatomical structure of a certain region in the target object with the target object; and control the storage to store a result of the mapping.

13. The image registering device of claim 11, further comprising a user input device configured to receive a user input of selecting the target object from the user, and the target object is selected by receiving the input of selecting the target object from a user.

14. The image registering device of claim 11, wherein the one or more processors are further configured to:

calculate a degree of correlation between the first cross-section image and the second cross-section image; and control the display to further display the second cross-section image and the degree of correlation.

15. The image registering device of claim 14, wherein the one or more processors are further configured to acquire the second volume data based on the second cross-section image, when the degree of correlation is a predetermined value or more.

16. The image registering device of claim 11, wherein the one or more processors are further configured to:

acquire a plurality of pieces of cross-section image data from the target object via the probe;

acquire information about a plurality of positions of the probe that correspond to the plurality of pieces of cross-section image data; and produce the second volume data based on the plurality of pieces of cross-section image data and the information about the plurality of positions of the probe.

17. The image registering device of claim 11, wherein the first image acquisition modality comprises a computed tomography (CT) image acquisition modality, and the second image acquisition modality comprises an ultrasound image acquisition modality.

18. The image registering device of claim 11, wherein the one or more processors are further configured to produce third volume data by registering the first volume data with the second volume data.

19. The image registering device of claim 18, wherein the one or more processors are further configured to:

acquire information about a current position of the probe;

select an image corresponding to the information about the current position of the probe from the third volume data; and control the display to further display the selected image.

20. An image registering device comprising:

a user input device configured to receive an input of selecting a target object from a user;

one or more processors configured to:

determine a reference image based on information about an anatomical structure stored in correspondence to the target object;

extract a first cross-section image corresponding to the reference image from first volume data about the target object, wherein the first volume data is acquired via a first image acquisition modality;

acquire second volume data about the target object, the second volume data including a second cross-section image corresponding to the reference image and position information of a probe, via a second image acquisition modality using the probe; and register the first volume data with the second volume data based on the first cross-section image, the second cross-section image, and the position information of the probe.

21. A non-transitory computer-readable recording medium having recorded thereon a computer program, which, when executed by a computer, performs the method of claim 1.

* * * * *